United States Patent [19]

Winston, Jr. et al.

[11] Patent Number: 5,342,626
[45] Date of Patent: Aug. 30, 1994

[54] COMPOSITION AND PROCESS FOR GELATIN-FREE SOFT CAPSULES

[75] Inventors: Philip E. Winston, Jr.; Frank J. Miskiel; Raymond C. Valli, all of San Diego, Calif.

[73] Assignee: Merck & Co., Inc., Rahway, N.J.

[21] Appl. No.: 53,578

[22] Filed: Apr. 27, 1993

[51] Int. Cl.$^5$ ............................................. A61K 9/62
[52] U.S. Cl. .................................... 424/461; 514/777; 514/780; 514/962; 426/573; 156/246; 53/454
[58] Field of Search ................ 424/461; 514/777, 780, 514/962; 427/3; 426/573

[56] References Cited

U.S. PATENT DOCUMENTS

| | | | |
|---|---|---|---|
| 4,326,052 | 4/1982 | Kang et al. | 536/1 |
| 4,326,053 | 4/1982 | Kang et al. | 536/1 |
| 4,377,636 | 3/1983 | Kang et al. | 435/101 |
| 4,385,123 | 5/1983 | Kang et al. | 435/253 |
| 4,647,470 | 3/1987 | Sanderson et al. | 426/573 |
| 4,746,528 | 5/1988 | Prest et al. | 426/573 |
| 5,112,445 | 5/1992 | Winston et al. | 162/178 |

FOREIGN PATENT DOCUMENTS 2219803A 12/1989 United Kingdom .

Primary Examiner—Thurman K. Page
Assistant Examiner—Jyothsna Venkat
Attorney, Agent, or Firm—Richard S. Parr; Melvin Winokur; Paul D. Matukaitis

[57] ABSTRACT

The present invention relates to a polymer composition comprised of gellan, carrageenan and mannan gums and a process for producing flexible films for encapsulation comprising the gellan, carrageenan and mannan gum composition. The mannan gums include the galactomannans and the glucomannans. Advantageously, soft capsules of the above composition are produced using the novel process. The composition comprises a blend of a gellan gum: (carrageenan/mannan gum) wherein the gellan gum concentration ranges from about 0.1 to 50 weight percent and the ratio of carrageenan/locust bean gum ranges from 3:1 to 1:3. Additional reagents are added to this gum blend to form a film-forming polymer composition useful in the production of gelatin-free capsules or microcapsules.

5 Claims, No Drawings

COMPOSITION AND PROCESS FOR GELATIN-FREE SOFT CAPSULES

BACKGROUND OF THE INVENTION

The present invention relates to a polymer composition comprised of gellan, carrageenan and mannan gums and a process for producing flexible films for encapsulation comprising the gellan, carrageenan and mannan gum composition. Advantageously, soft capsules of the above composition are produced using the novel process.

The art reveals that processes and compositions for encapsulation or producing soft capsules generally are composed of gelatin or animal based gels. Soft capsules have primarily been made from low bloom gelatin which melts at low temperatures so that in the manufacturing process two sheets of gelatin are sealed simultaneously with the filling of the capsule. There is a need, however, for producing soft capsules containing liquid or solid contents selected from food or nutritional supplements including vitamins or minerals and the like wherein the capsules are edible and derived from non animal based sources and the capsules can be produced on the existing machinery which is utilized to produce the gelatin based capsules and films. Various polysaccharides and various processes for making them and using them are known. See: U.S. Pat. Nos. 4,326,052; 4,326,053; 4,377,636; 4,385,123; 4,647,470; 4,746,528 and 5,112,445. U.S. Pat. No. 4,746,528 describes combinations of gellan, xanthan gum and a galactomannan and/or glucomannan gum used to produce elastic gels. U.S. Pat. No. 4,647,470 describes blends of low-acetyl gellan gum with xanthan gum and locust bean gum, konjak, tara or cassia gums which are useful for modifying the brittleness of gellan food products. Gelled food product compositions comprising blends of gellan gum/K-carrageenan gum and mannan gums in weight ratios of about 80:20 to 10:90 of K-carrageenan to mannan and about 95:5 to 20:80 of gellan gum to (K-carrageenan/mannan) are known. See GB 2219803 A.

The art also reveals that heretofore many of the film-forming water soluble materials have high melting temperatures and/or decompose at melting temperatures thus rendering them unsuitable for producing non-animal based capsules. There is an additional need to provide soft capsules which may be utilized to encapsulate bath oils and the like wherein the capsular material is composed of non-gelatin based sources and is water soluble. There is an additional need for novel processes related to the production of non-animal based soft capsules or flexible films such as those claimed and disclosed in the present invention. The present invention therefore satisfies the need for producing capsules wherein the particular non-animal derived compositions comprise suitable material which has the essential low melting and stability characteristics of the animal derived gelatins and thus can be produced on existing capsule machinery.

SUMMARY OF THE INVENTION

The present invention relates to a polymer composition comprised of gellan, carrageenan and mannan gums and a process for producing flexible films for encapsulation, specifically soft capsules. There is a need for non-animal sourced, i.e. gelatin-free, encapsulating polymer systems that will remelt under controlled conditions to form soft capsules to seal the encapsulated contents that may be selected from liquid or solid active or inactive ingredients within two polymer sheets. The present invention therefore involves a polymer composition and a process for producing a complete capsule wherein the capsule contains the selected contents including active and inactive ingredients in solid or liquid form which may then readily be administered to or taken by a target organism.

The total polymer concentration of the film-forming composition ranges from 1 to 10 weight percent of the total weight of the capsule. The gellan gum concentration ranges from about 0.1 to 50 weight percent and the carrageenan to mannan gum weight ratio ranges from 3:1 to 1:3. In order to achieve remelting of the film composition at a soft capsule processing temperature of less than 100° C., sufficient water must be available to inhibit polymer association and subsequent increase in the melting temperature above 100° C.

DETAILED DESCRIPTION OF THE INVENTION

The present invention relates to a polymer composition comprised of gellan, carrageenan and mannan gums wherein the mannan gums are selected from a galactomannan or a glucomannan and a process for producing flexible films for encapsulation, specifically soft capsules. There is a need for non-animal sourced, i.e. gelatin-free, encapsulating polymer systems that will remelt under controlled conditions to form soft capsules to seal the encapsulated contents that may be selected from liquid or solid active or ingredients within two polymer sheets. The present invention therefore involves a polymer composition and a process for producing a complete capsule wherein the capsule contains the selected contents including active and inactive ingredients in solid or liquid form which may then readily be administered to or taken by a target organism. Advantageously, a gum-blend composition comprising a gellan gum: (carrageenan gum/mannan gum) wherein the gellan gum concentration ranges from about 0.1 to 50 weight percent and the ratio of carrageenan/mannan gum ranges from 3:1 to 1:3 is used in the present invention to form the various film-forming polymer compositions. The present invention also relates to a gum-blend composition comprising a gellan gum: (carrageenan gum/mannan gum) wherein the gellan gum concentration ranges from about 0.1 to about 19% weight percent and the ratio of carrageenan/mannan gum ranges from 3:1 to 1:3.

The total polymer concentration of the film-forming composition ranges from 1 to 10 weight percent of the total weight of the capsule. The gellan gum concentration ranges from about 0.1 to 50 weight percent and the carrageenan to mannan gum weight ratio ranges from 3:1 to 1:3. In order to achieve remelting of the film composition at a soft capsule processing temperature of less than 100° C., sufficient water must be available to inhibit polymer association and subsequent increase in the melting temperature above 100° C.

The melting property of the flexible film disclosed in the present application is critical to the proper sealing of the capsules produced during production of said soft capsules. The present invention makes use of a unique combination of hydrocolloids which interact to give synergistic film properties. Furthermore, by controlling the solids content of the film during the encapsulation process, a melting temperature of less than 100° C. for the polymer composition within the scope of the present invention is achieved. The compositions and processes of the present invention have numerous advantages including biodegradability, strength, thermal reversibility, water solubility and reduced processing time.

Gellan gum refers to the extracellular polysaccharide obtained by the aerobic fermentation of the microorganism, *Pseudomonas elodea*, in a suitable nutrient medium. Various forms of gellan gum have been described and may be utilized in the present invention. These gums include native, deacetylated, deacetylated clarified, partially deacetylated, and partially deacetylated clarified. As used hereafter, "gellan gum" shall refer to low acetyl (LA) gellan gum which has an acetyl level of 0.3 to 0% weight and to high acetyl (HA) gellan gum which has an acetyl level greater than 0.3% weight and to blends or combinations of LA and HA gellan gum.

Mannan gums include the galactomannan gums and the glucomannan gums or mixtures thereof. Locust bean gum (lbg) is an extract of the locust bean or carob, *Ceratonia siligua* and is a member of the galactomannan class. It is commercially available and used as a stabilizer in various food products. Glucomannans are also included within the scope of the present invention and may be selected from, for example, konjak gum, tara and/or cassia gums. Konjac or konjac gum is a glucomannan extracted from the plant *Amorphophallus konjac*. Tara gum is a vegetable gum derived from the seed of the legume *Cesalpinia spinosa*. Cassia gum is a pod extract derived from *Cassia occidentalis* or fistula.

k-carrageenan is a hydrocolloid obtained by extraction with water or other polar solvents from some members of the algae class Rhodophyceae (red algae) and consists of a mixture of the ammonium, calcium, magnesium, potassium, and sodium esters of galactose and 3-6-anhydrogalactose copolymers. Carrageenans include the κ, λ, and τ forms. These additives are used predominantly as suspending or gelling agents in the pharmaceutical or food industries.

The present invention is directed to a tri-combination of the above components in particular ratios which under the appropriate conditions as described herein may be utilized to produce polymeric films useful in producing non-gelatin capsules which are soft and water soluble. The mannan gum component is preferably selected from either locust bean gum or konjak gum. Of course, mixtures of the mannan gums may also be utilized in the present invention. The tri-combination may be formulated and is preferably formulated in the following ratios for the film-forming polymeric compositions:

| gellan gum | k-carrageenan | locust bean gum |
|---|---|---|
| 0.100 | 0.225 | 0.675 |
| 0.100 | 0.675 | 0.225 |
| 0.100 | 2.475 | 0.7425 |
| 0.800 | 1.900 | 0.950 |
| 5.000 | 1.250 | 3.750 |
| 5.000 | 3.750 | 1.250 |

This tri-gum combination or a combination wherein a mannan gum such as konjak gum is substituted for the locust bean gum or any tri-combination within the scope of the present invention may be further combined with a salt such as potassium citrate and additional ingredients such as sorbitol, glycerine, corn syrup and deionized water to form a film-forming polymeric composition. Sodium citrate and potassium chloride may also be added to form an aqueous composition useful in the preparation of film-forming compositions. Sequestrants selected from a sodium or potassium phosphate or citrate salt or combinations thereof may be utilized in the present invention. For example, sodium phosphate and/or sodium citrate may be added to the composition and are useful in chelating the divalent ions such as magnesium and calcium and allow complete hydration of the gellan gum. The added potassium salt level in the gum/film forming composition is useful as it relates to the melting and setting temperature of the film.

The following gelling salts may be utilized in the present invention: sodium chloride, sodium sulfate, and other sodium salts of appropriate organic or inorganic acids. Potassium sulfate and other potassium salts of appropriate organic or inorganic acids may also be utilized as gelling salts in the present invention. One skilled in the art will appreciate that under certain circumstances and conditions, certain ions are necessary to gel certain gums such as the kappa form of a carrageenan gum. Therefore, when κ-carrageenan is used, potassium ions must be present to obtain the maximum performance of the gum. Furthermore, the use of mono- or di-valent ions to gel gellan gum is determined by the requirement of gel texture and modulus.

A process for preparing compositions within the scope of the present invention and for manufacturing soft capsules from the compositions comprises the steps of:

(1) A tri-gum blend comprising gellan gum, locust bean gum and k-carrageenan gum in the relative ratios as described above such as, for example, (a) low-acyl gellan gum with a relative weight percentage of about 20%; (b) k-carrageenan gum with a relative weight percentage of about 50%; (c) locust bean gum with a relative weight percentage of about 25%; and a salt such as potassium citrate in a relative weight percentage of about 9% wherein the potassium citrate is used as a sequestrant/gelling salt is mixed into cold (20°–30° C.) deionized water and then the ingredients sorbitol, glycerine and corn syrup are added with agitation. The plasticizers or other reagents useful in the present invention may be selected from sorbitol, glycerine, propylene glycol, polyethylene glycol, corn syrup, sucrose, fructose or combinations thereof. The mixture is then heated to a temperature of about 75°–100° C. Advantageously, the mixture is heated to 90° C. with agitation and held at this temperature for about 10 minutes;

(2) The hot solution produced in step 1 is then, for example, transferred to an encapsulation machine wherein a 30–40 mil film is formed on rotating steel drums. Two films thus formed on the steel drums proceed through rotating dies that are designed to simultaneously form, cut and fill various sized and shaped capsules. The fill material may be either solid or liquid material. The edges of the capsule formed in this process are heat and pressured sealed and the filled capsules are then washed, dried to a pre-determined moisture content such as 3–4% and packaged. The moisture content of the film during the encapsulation process controls the melting temperature and the proper sealing of the capsules.

In the above process, the locust bean gum can readily be substituted with a mannan gum such as konjak gum or mixtures of locust bean gums and konjak gums in a ratio of 1:100 to 100:1 Gelatin free soft capsules utilizing these compositions may readily be prepared.

EXAMPLES

The following gum-blends and/or gum blend aqueous compositions may readily be prepared. The relative ratios of the gums and additional reagents are generally expressed in relative weight percentages. The variations in relative composition may also be reflected in simple weight ratio comparisons. The following examples are reflected in weight percentages and reflect the number of grams used to prepare the compositions.

When water is added to form the film-forming polymeric composition, the units in the following examples are expressed in either weight percentages or in milliliters (mls). It is understood, however, that any quantities within the claimed ratios may be prepared depending upon the needs of the preparer and upon the quantity needed to manufacture.

EXAMPLE 1

|  | wt % |
| --- | --- |
| Low-acyl gellan gum | 19.05% |
| k-carrageenan | 47.62% |
| locust bean gum | 23.81% |
| Potassium citrate | 9.52% |

EXAMPLE 2

| High-acyl gellan gum | 19.05% |
| --- | --- |
| k-carrageenan | 47.62% |
| locust bean gum | 23.81% |
| Potassium citrate | 9.52% |

The gum blends such as those described in Examples 1 or 2 or other gum blends within the scope of the present invention may be further combined with additional ingredients to form a film-forming polymer composition. The following examples are representative of those film-forming polymeric compositions useful for the production of capsules and the like and are not to be construed as limiting the scope of the present invention.

EXAMPLE 3

| Gum blend (EX 1) | 4.00% |
| --- | --- |
| Sorbitol | 5.67% |
| Glycerine | 5.67% |
| Corn syrup | 5.67% |
| Deionized water | 78.99% |

EXAMPLE 4

| Gum blend (EX 2) | 4.00% |
| --- | --- |
| Sorbitol | 5.67% |
| Glycerine | 5.67% |
| Corn syrup | 5.67% |
| Deionized water | 78.99% |

In addition to the examples described above, the following film-forming polymeric compositions may also be prepared.

EXAMPLE 5

| Gellan gum (LA) | 0.66% |
| --- | --- |
| k-carrageenan | 0.66% |
| locust bean gum | 0.66% |
| Glycerine | 0.60% |
| sodium citrate | 0.10% |
| Potassium chloride | 0.10% |
| Deionized water | 97.22% |

EXAMPLE 6

| Gellan gum (HA) | 0.40% |
| --- | --- |
| k-carrageenan | 1.00% |
| Locust bean gum | 1.00% |
| Polydextrose | 13.40% |
| Sorbitol | 4.00% |
| Sodium citrate | 0.10% |
| Potassium chloride | 0.10% |
| Deionized water | 80.0% |

EXAMPLE 7

| Gellan gum (HA) | 0.29% |
| --- | --- |
| k-carrageenan | 1.62% |
| locust bean gum | 0.81% |
| Sorbitol | 6.00% |
| Glycerine | 6.00% |
| corn syrup | 6.00% |
| Potassium citrate | 0.29% |
| Deionized water | 78.99% |

EXAMPLE 8

| Gellan gum (LA) | 0.66% |
| --- | --- |
| k-carrageenan | 1.33% |
| konjac | 2.33% |
| Glycerine | 9.97% |
| Sodium citrate | 0.30% |
| Deionized water | 85.41% |

The physical properties of examples 3–7 are listed below and demonstrate the effectiveness of the films prepared within the scope of the present invention. In addition to the described physical properties, the capsules or other products formed from the film-forming compositions are particularly useful because they provide a gelatin-free polymeric composition.

| Example Number | Tensile Strength (psi) | Elongation at break (%) |
| --- | --- | --- |
| 3 | 525 | 143 |
| 4 | 531 | 177 |
| 5 | 2423 | 78 |
| 6 | 1087 | 107 |
| 7 | 396 | 122 |

Films of the example solutions while hot were cast with a knife blade set at 100 mil clearance and allowed to air dry 24 hours at 60% relative humidity and 22° C. prior to being tested on an INSTRON Model 1011 tensile-testing instrument.

EXAMPLE 9

The composition within the scope of the present invention was prepared according to the following process:

(1) A tri-gum blend comprising gellan gum, locust bean gum and K-carrageenan gum in the relative ratios as described above such as, for example, (a) high-acyl gellan gum (0.29 grams); (b) K-carrageenan gum (1.62 grams); (c) locust bean gum (0.81 grams); and a salt such as potassium citrate (0.29 grams) wherein the potassium citrate is used as a sequestrant/gelling salt was mixed into cold (20°–30° C.) deionized water (about 80 mls) and then the ingredients sorbitol (6 grams), glycerine (6 grams) and corn syrup (6 grams) were added with agitation. The mixture was then heated to a temperature of about 90° C. with agitation and held at this temperature for about 10 minutes;

(2) The hot solution produced in step 1 was then, for example, transferred to an encapsulation machine well known to those skilled in the art which was first developed in 1932 by R. P. Scherer, wherein a 30–40 mil (0.030–0.040 inches) (a mil is defined as 0.001 inch and is a common measurement of film thickness) film was formed on rotating steel drums. The rotating steel drums can vary in size from 12 inches in diameter to 30 inches or more depending on the size of the encapsulation machine. The width of the rotating steel cylinder can also vary from 6–12 inches. The drums are hollow and can be heated or cooled by injecting liquids within the drum. The two films thus formed on the steel drums proceed through counter-rotating dies that were designed to simultaneously form, cut and fill various sized and shaped capsules. The counter-rotating dies are normally made of solid brass and are cylinders approximately six inches in diameter and 12 inches long depending on the width of the encapsulating film. Various shapes of capsules may be cut into the brass circumference of the die. The fill material may be either solid or liquid material.

The fill material used in the above examples was mineral oil and fragrances since this material may be utilized in the production of bath beads which generally contain mineral oil and fragrances. Of course, the fill-material may be selected from any desired known solid or liquid material which the manufacturer deems necessary. The edges of the capsule formed in this process were heat and pressured sealed at a temperature range of 75°–85° C. and a pressure range of 0.1–2 psi and the filled capsules were then washed with a petroleum based solvent to remove the traces of mineral oil, dried to a pre-determined moisture content of 3–4% and packaged. The moisture content of the film during the encapsulation process controls the melting temperature and the proper sealing of the capsules.

Capsules produced in the above process can further be utilized in a method of treating a nutritional deficiency in a mammalian organism in need of treatment thereof comprising administering to said mammalian organism an edible soft capsule of the composition according to claim 1, wherein the capsule contains contents selected from an essential vitamin or nutrient and a method of administering a bath capsule to a bath comprising adding to said bath a soft capsule of a water soluble composition according to claim 1, wherein the capsule contains contents selected from a bath oil or detergent or perfume. Of course, additional ingredients may be added to the capsule contents during the manufacturing process to produce a suitable target capsule.

Gelatin-free carbonless paper utilizing microcapsules containing dyes may readily be prepared using the claimed composition and process. Furthermore, the present invention also encompasses microencapsulation of any water-immiscible liquids to, for example, mask unpleasant tastes or to protect substances from oxidation and also to allow controlled release of encapsulated material and physical separation of reactive materials.

What is claimed is:

1. A gelatin-free soft capsule comprising from 1 to 10 weight percent of a gum-blend composition which comprises a gellan gum: (carrageenan gum/mannan gum) wherein the gellan gum concentration ranges from about 0.1 to 50 weight percent and the ratio of carrageenan/mannan gum ranges from 3:1 to 1:3 and one or more gelling salts.

2. The gelatin-free soft capsule according to claim 1 wherein the gellan gum concentration ranges from 0.1 to 50 weight percent of the gum-blend composition and the carrageenan to mannan gum weight ratio ranges from 3:1 to 1:3 wherein the mannan gum is selected from the group consisting of locust bean gum, konjac gum, tara gum, cassia gum and combinations thereof and the gelling salts are selected from the group consisting of sodium citrate, potassium citrate, and potassium chloride.

3. The gelatin-free soft capsule according to claim 2, further comprising a plasticizer selected from the group consisting of sorbitol, glycerine, propylene glycol, polyethylene glycol, corn syrup, sucrose, fructose and combinations thereof.

4. A process for producing a gelatin-free soft capsule, comprising the steps of:
   (a) transferring a hot aqueous mixture containing the gum blend composition according to claim 1 to a plurality of rotating drums;
   (b) casting a 30–40 mil film on the plurality of rotating drums;
   (c) passing at least two of the 30–40 mil films over rotating dies;
   (d) simultaneously forming, filling, heat-sealing and cutting capsules; and
   (e) washing and drying said capsules.

5. A process according to claim 4, wherein the capsule contains contents selected from a group consisting of a bath oil, detergent and perfume.

* * * * *